US008790880B2

(12) United States Patent
Davis et al.

(10) Patent No.: US 8,790,880 B2
(45) Date of Patent: Jul. 29, 2014

(54) CYSTEINE PROTEASE CWP84 (CD2787) AS A DIAGNOSTIC MARKER FOR *CLOSTRIDIUM DIFFICILE*

(71) Applicant: Techlab, Inc., Blacksburg, VA (US)

(72) Inventors: Manli Y. Davis, Christiansburg, VA (US); David M. Lyerly, Radford, VA (US); Tracy D. Wilkins, Riner, VA (US)

(73) Assignee: Techlab, Inc., Blacksburg, VA (US)

( * ) Notice: Subject to any disclaimer, the term of this patent is extended or adjusted under 35 U.S.C. 154(b) by 0 days.

(21) Appl. No.: 13/626,298

(22) Filed: Sep. 25, 2012

(65) Prior Publication Data

US 2013/0130281 A1 May 23, 2013

Related U.S. Application Data

(60) Provisional application No. 61/539,209, filed on Sep. 26, 2011.

(51) Int. Cl.
*G01N 33/53* (2006.01)
*G01N 33/554* (2006.01)

(52) U.S. Cl.
USPC .............................. 435/7.1; 435/7.2; 435/7.32

(58) Field of Classification Search
None
See application file for complete search history.

(56) References Cited

U.S. PATENT DOCUMENTS

| 5,231,003 A * | 7/1993 | Coughlin et al. ............ 435/7.32 |
| 2010/0291152 A1 | 11/2010 | Shone et al. |
| 2011/0020356 A1 | 1/2011 | Fang et al. |

FOREIGN PATENT DOCUMENTS

WO 2006058286 A3 12/2006

OTHER PUBLICATIONS

Pechine et al (Journal of Clinical Microbiology vol. 43, No. 10, pp. 5018-5025, Oct. 2005).*
Schroeder, M.S., *Clostridium difficile*-associated diarrhea. Am Fam Physician, 2005. 71(5): p. 921-8.
Aronsson, B., R. Mollby, and C.E. Nord, Antimicrobial agents and *Clostridium difficile* in acute enteric disease: epidemiological data from Sweden, 1980-1982. J Infect Dis, 1985. 151(3): p. 476-81.
Zilberberg, M.D., et al., *Clostridium difficile*-associated disease and mortality among the elderly critically ill. Crit Care Med, 2009. 37(9): p. 2583-9.
Kim, K.H., et al., Isolation of *Clostridium difficile* from the environment and contacts of patients with antibiotic-associated colitis. J Infect Dis, 1981. 143(1): p. 42-50.
McGlone, S.M., et al, The economic burden of *Clostridium difficile*. Clin Microbiol Infect, 2011.
Redelings, M.D., F. Sorvillo, and L. Mascola, Increase in *Clostridium difficile*-related mortality rates, United States, 1999-2004. Emerg Infect Dis, 2007. 13(9): p. 1417-9.
George, W.L., et al., Selective and differential medium for isolation of *Clostridium difficile*. J Clin Microbiol, 1979. 9(2): p. 214-9.
Lyerly, D.M., L.A. Barroso, and T.D. Wilkins, Identification of the latex test-reactive protein of *Clostridium difficile* as glutamate dehydrogenase. J Clin Microbiol, 1991. 29(11): p. 2639-42.
Orellana-Miguel, M.A., et al., Algorithm proposal based on the *C. Diff* Quik Chek Complete ICT device for detecting *Clostridium difficile* infection. Enferm Infeec Microbiol Clin, 2012.
Lee, J.H., et al., Evaluation of the diagnostic algorithm consisting of enzyme immunoassay for toxins and polymerase chain reaction, for the diagnosis of *Clostridium difficile*-associated diarrhoea. Scand J infect Dis, 2012.
Vasoo, S., et al., Cost-effectiveness of a modified two-step algorithm using a combined glutamate dehydrogenase/toxin enzyme immunoassay and real-time PCR for the diagnosis of *Clostridium difficile* infection. J Microbiol Immunol Infect, 2012.
Calabi, E., et al., Binding of *Clostridium difficile* surface layer proteins to gastrointestinal tissues, Infect Immun, 2002. 70(10): p. 5770-8.
Tasteyre, A., et al., Role of FliC and FliD flagellar proteins of *Clostridium difficile* in adherence and gut colonization. Infect Immun, 2001. 69(12): p. 7937-40.
Hennequin, et al., GroEL (Hsp60) of *Clostridium difficile* is involved in cell adherence. Microbiology, 2001. 147(Pt 1): p. 87-96.
Hennequin, C., et al., Identification and characterization of a fibronectin-binding protein from *Clostridium difficile*. Microbiology, 2003. 149(Pt 10): p. 2779-87.
Masuda, K., M. Itoh, and T. Kawata, Characterization and reassembly of a regular array in the cell wall of *Clostridium difficile* GAI 4131. Microbiol Immunol, 1989. 33(4): p. 287-98.
Deneve, C., et al., Effects of subinhibitory concentrations of antibiotics on colonization factor expression by moxifloxacin-susceptible and moxifloxacin-resistant *Clostridium difficile* strains. Antimicrob Agents Chemother, 2009. 53(12): p. 5155-62.
de la Riva, L., et al., Roles of Cysteine Proteases Cwp84 and Cwp13 in Biogenesis of the Cell Wall of *Clostridium difficile*. J Bacteriol, 2011. 193(13): p. 3276-85.
Dang, T.H., et al., Chemical probes of surface layer biogenesis in *Clostridium difficile*, ACS Chem Biol, 2010. 5(3): p. 279-85.
Poilane, I., et al., Protease activity of *Clostridium difficile* strains. Can J Microbiol, 1998. 44(2): p. 157-61.
Montes, D.C., et al., Localization of the *Clostridium difficile* cysteine protease Cwp84 and insights into its maturation process. J. Bacteriol, 2011.
Janoir, C., et al., Cwp84, a surface-associated protein of *Clostridium difficile*, is a cystein protease with degrading activity on extracellular matrix proteins. J Bacteriol, 2007. 189(20): p. 7174-80.
Calabi E. and N. Fairweather Patterns of seouence conservation in the S-Layer proteins and related sequences in *Clostridium difficile*. J Bacteriol, 2002. 184(14): p. 3886-97.
Fagan, R.P. and N.F. Fairweather, *Clostridium difficile* has two parallel and essential Sec secretion systems. J Biol Chem, 2011.

(Continued)

*Primary Examiner* — Albert Navarro
(74) *Attorney, Agent, or Firm* — Shook, Hardy & Bacon L.L.P.

(57) ABSTRACT

Accurate and fast detection of the presence of *Clostridium difficile* (*C. difficile*) disease is crucial for the proper treatment of patients with *C. difficile* infection. Present tests detecting the presence of *C. difficile* disease are fast and cost effective, but are not very sensitive. Using an ELISA including Cell Wall Protein 84 (Cwp84) increases the sensitivity of the ELISA. Cwp84 may be used alone or in combination with other markers to support a diagnosis of *C. difficile*-associated disease.

17 Claims, 2 Drawing Sheets

(56) References Cited

OTHER PUBLICATIONS

Savanau-Lacomme, M.P., et al., Transcription and analysis of polymorphism in a cluster of genes encoding surface-associated proteins of *Clostridium difficile*. J Bacteriol, 2003. 185(15): p. 4461-70.

Freeman, J. and M.H Wilcox, Antibiotics and *Clostridium difficile*. Microbes Infect, 1909. 1(5): p. 377-84.

Spencer, R.C., The role of antimicrobial agents in the aetiology of *Clostridium difficile*-associated disease. J Antimicrob Chemother, 1998. 41 Suppl C: p. 21-7.

Pepin, J., et al., Emergence of fluoroquinolones as the predominant risk factor for *Clostridium difficile*-associated diarrhea: a cohort study during an epidemic in Quebec. Clin Infect Dis, 2005. 41(9): p. 1254-60.

Deneve, C., et al., Antibiotics involved in *Clostridium difficile*-associated disease increase colonization factor gene expression. J Med Microbial, 2008. 57(Pt 6): p. 732-8.

Deneye C. et al., New trends in *Clostridium difficile* virulence and pathogenesis. Int J Antimicrob Agents, 2009 33 Suppl 1. p. S24-8.

Stubbs, S.L., et al., PCR targeted to the 16S-23S rRNA gene intergenic spacer region of *Clostridium difficile* and construction of a library consisting of 116 different PCR ribotypes. J Clin Microbiol, 1999. 37(2): p. 461-3.

Quinn et al. *C. Diff.* Quik Chek complete enzyme immunoassay, provides a reliable first-line method for detection of *Clostridium difficile* in stool specimens. J Clin Microbiol Feb. 2010 vol. 48 No. 2 pp. 603-605. Especially p. 603 col. 1 para 1-2; p. 604 fig 1 p. 605 col. 1 para 4.

Pechine et al. Variability of *Clostridium difficile* surface proteins and specific serum antibody response in patients with *Clostridium difficile*-associated disease. J Clin Mibrobiol Oct. 2005 vol. 43 No. 10 pp. 5018-5025. Especially p. 5019 col. 1 pare 2, p. 5020 col. 2 para 4-6, p. 5022 fig. 3D.

de la Riva et al. Rolse of cysteine proteases Cwp84 and cwp13 in biogenesis of the cell wall of *Clostridium difficile*. J. Bacteriol Jul. 2011 vol. 193 No. 13 pp. 3276-3285. Especially p. 3279 col. 1 para. 4.

PCT/US12/57347, International Search Report and Written Opinion, dated Jan. 24, 201 3, 11 pages.

* cited by examiner

```
  1 mrkykskkls kllalltvcf livstipvsa enhktldgve taeysesylq yledvkngdt
 61 akyngvipfp hemegttlrn kgrsslpsay kssvaynpmd lglttpaknq gslntcwsfs
121 gmstleaylk lkgygtydls eehlrwwatg gkygwnlddm sgssnvtaig yltawagpkl
181 ekdipynlks eaqgatkpsn mdtaptqfnv tdvvrlnkdk etvknaimqy gsvtsgyahy
241 styfnkdeta ynctnkrapl nhavaivgwd dnyskdnfas dvkpesngaw lvksswgefn
301 smkgffwisy edktlltdtd nyamksvskp dsdkkmyqle yaglskimsn kvtaanvfdf
361 srdsekldsv mfetdsvgak yevyyapvvn gvpqnnsmtk lasgtvsysg yinvptnsys
421 lpkgkgaivv vidntanpnr ekstlayetn idayylyeak anlgesyilq nnkfedinty
481 sefspcnfvi kaitktssgq atsgesltga dryetavkvs qkgwtsssqna vlvngdaivd
541 altatpftaa idspilltgk dnldsktkae lqrlgtkkvy liggenslsk nvqtqlsnmg
601 isverisgsd ryktsislaq klnsiksvsq vavangvngl adaisvgaaa adnnmpiilt
661 nekselqgad eflnsskitk syiiggtatl ssnlesklsn ptrlagsnrn etnakiiidkf
721 ypssdlkyaf vvkdgsksqg dlidglavga lgaktdspvv lvgnkldesq knvlkskkie
781 tpirvggngn esafnelntl lgk
```

FIG. 1

| | | ETHANOL SHOCK CULTURE | |
|---|---|---|---|
| | | + | - |
| ANTI-CWP84 ELISA | + | 29 | 0 |
| | - | 5 | 30 |

| | | ETHANOL SHOCK CULTURE | |
|---|---|---|---|
| | | + | - |
| ANTI-GDH ALONE | + | 20 | 0 |
| | - | 25 | 0 |

| | | ETHANOL SHOCK CULTURE | |
|---|---|---|---|
| | | + | - |
| ANTI-CWP84 + ANTI-GDH ELISA | + | 25 | 0 |
| | - | 20 | 0 |

SEQUENCE LISTING

```
<160> NUMBER OF SEQ ID NOS: 1

<210> SEQ ID NO 1
<211> LENGTH: 803
<212> TYPE: PRT
<213> ORGANISM: Clostridium difficile strain 630
<220> FEATURE:
<221> NAME/KEY: Cwp84
<222> LOCATION: (1)..(803)

<400> SEQUENCE: 1

Met Arg Lys Tyr Lys Ser Lys Lys Leu Ser Lys Leu Leu Ala Leu Leu
1               5                   10                  15

Thr Val Cys Phe Leu Ile Val Ser Thr Ile Pro Val Ala Ala Glu Asn
            20                  25                  30

His Lys Thr Leu Asp Gly Val Glu Thr Ala Glu Tyr Ser Glu Ser Tyr
        35                  40                  45

Leu Gln Tyr Leu Glu Asp Val Lys Asn Gly Asp Thr Ala Lys Tyr Asn
```

```
                50              55              60
Gly Val Ile Pro Phe Pro His Glu Met Glu Gly Thr Thr Leu Asn Asn
 65              70              75              80
Lys Gly Arg Ser Ser Leu Pro Ser Ala Tyr Lys Ser Val Ala Tyr
                85              90              95
Asn Pro Met Asp Leu Gly Leu Thr Thr Pro Ala Lys Asn Gln Gly Ala
                100             105             110
Leu Asn Thr Cys Trp Ser Phe Ala Gly Met Ser Thr Leu Glu Ala Tyr
                115             120             125
Leu Lys Leu Lys Gly Tyr Gly Thr Tyr Asp Leu Ser Glu Glu His Leu
                130             135             140
Arg Trp Trp Ala Thr Gly Gly Lys Tyr Gly Trp Asn Leu Asp Asp Met
145             150             155             160
Ser Gly Ser Ser Asn Val Thr Ala Ile Gly Tyr Leu Thr Ala Trp Ala
                165             170             175
Gly Pro Lys Leu Glu Lys Asp Ile Pro Tyr Asn Leu Lys Ser Ala Ala
                180             185             190
Gln Gly Ala Thr Lys Pro Ser Asn Met Asp Thr Ala Pro Thr Gln Phe
                195             200             205
Asn Val Thr Asp Val Val Arg Leu Asn Lys Asp Lys Glu Thr Val Lys
                210             215             220
Asn Ala Ile Met Gln Tyr Gly Ser Val Thr Ser Gln Tyr Ala His Tyr
225             230             235             240
Ala Thr Tyr Phe Asn Lys Asp Glu Thr Ala Tyr Asn Cys Thr Asn Lys
                245             250             255
Arg Ala Pro Leu Asn His Ala Val Ala Ile Val Gly Trp Asp Asp Asn
                260             265             270
Tyr Ser Lys Asp Asn Phe Ala Ser Asp Tyr Lys Pro Glu Ser Asn Gly
                275             280             285
Ala Trp Leu Val Lys Ser Ser Trp Gly Glu Phe Asn Ser Met Lys Gly
                290             295             300
Phe Phe Trp Ile Ser Tyr Glu Asp Lys Thr Leu Leu Thr Asp Thr Asp
305             310             315             320
Asn Tyr Ala Met Lys Ser Val Ser Lys Pro Asp Ser Asp Lys Lys Met
                325             330             335
Tyr Gln Leu Glu Tyr Ala Gly Leu Ser Lys Ile Met Ser Asn Lys Val
                340             345             350
Thr Ala Ala Asn Val Phe Asp Phe Ser Arg Asp Ser Glu Lys Leu Asp
                355             360             365
Ser Val Met Phe Glu Thr Asp Ser Val Gly Ala Lys Tyr Glu Val Tyr
                370             375             380
Tyr Ala Pro Val Val Asn Gly Val Pro Gln Asn Asn Ser Met Thr Lys
385             390             395             400
Leu Ala Ser Gly Thr Val Ser Tyr Ser Gly Tyr Ile Asn Val Pro Thr
                405             410             415
Asn Ser Tyr Ser Leu Pro Lys Gly Lys Gly Ala Ile Val Val Val Ile
                420             425             430
Asp Asn Thr Ala Asn Pro Asn Arg Glu Lys Ser Thr Leu Ala Tyr Glu
                435             440             445
Thr Asn Ile Asp Ala Tyr Tyr Leu Tyr Glu Ala Lys Ala Asn Leu Gly
                450             455             460
Glu Ser Tyr Ile Leu Gln Asn Asn Lys Phe Glu Asp Ile Asn Thr Tyr
465             470             475             480
```

-continued

```
Ser Glu Phe Ser Pro Cys Asn Phe Val Ile Lys Ala Ile Thr Lys Thr
                485                 490                 495

Ser Ser Gly Gln Ala Thr Ser Gly Glu Ser Leu Thr Gly Ala Asp Arg
            500                 505                 510

Tyr Glu Thr Ala Val Lys Val Ser Gln Lys Gly Trp Thr Ser Ser Gln
        515                 520                 525

Asn Ala Val Leu Val Asn Gly Asp Ala Ile Val Asp Ala Leu Thr Ala
    530                 535                 540

Thr Pro Phe Thr Ala Ala Ile Asp Ser Pro Ile Leu Leu Thr Gly Lys
545                 550                 555                 560

Asp Asn Leu Asp Ser Lys Thr Lys Ala Glu Leu Gln Arg Leu Gly Thr
                565                 570                 575

Lys Lys Val Tyr Leu Ile Gly Gly Glu Asn Ser Leu Ser Lys Asn Val
            580                 585                 590

Gln Thr Gln Leu Ser Asn Met Gly Ile Ser Val Glu Arg Ile Ser Gly
        595                 600                 605

Ser Asp Arg Tyr Lys Thr Ser Ile Ser Leu Ala Gln Lys Leu Asn Ser
    610                 615                 620

Ile Lys Ser Val Ser Gln Val Ala Val Ala Asn Gly Val Asn Gly Leu
625                 630                 635                 640

Ala Asp Ala Ile Ser Val Gly Ala Ala Ala Asp Asn Asn Met Pro
                645                 650                 655

Ile Ile Leu Thr Asn Glu Lys Ser Glu Leu Gln Gly Ala Asp Glu Phe
                660                 665                 670

Leu Asn Ser Ser Lys Ile Thr Lys Ser Tyr Ile Ile Gly Gly Thr Ala
            675                 680                 685

Thr Leu Ser Ser Asn Leu Glu Ser Lys Leu Ser Asn Pro Thr Arg Leu
        690                 695                 700

Ala Gly Ser Asn Arg Asn Glu Thr Asn Ala Lys Ile Ile Asp Lys Phe
705                 710                 715                 720

Tyr Pro Ser Ser Asp Leu Lys Tyr Ala Phe Val Val Lys Asp Gly Ser
                725                 730                 735

Lys Ser Gln Gly Asp Leu Ile Asp Gly Leu Ala Val Gly Ala Leu Gly
            740                 745                 750

Ala Lys Thr Asp Ser Pro Val Val Leu Val Gly Asn Lys Leu Asp Glu
        755                 760                 765

Ser Gln Lys Asn Val Leu Lys Ser Lys Lys Ile Glu Thr Pro Ile Arg
    770                 775                 780

Val Gly Gly Asn Gly Asn Glu Ser Ala Phe Asn Glu Leu Asn Thr Leu
785                 790                 795                 800

Leu Gly Lys
```

CYSTEINE PROTEASE CWP84 (CD2787) AS A DIAGNOSTIC MARKER FOR *CLOSTRIDIUM DIFFICILE*

CROSS-REFERENCE TO RELATED APPLICATIONS

This application claims the benefit of U.S. Provisional Application No. 61/539,209 filed Sep. 26, 2011, which is entirely incorporated herein by reference.

BACKGROUND

*Clostridium difficile* (*C. difficile*) is the most common cause of nosocomial diarrhea and accounts for about 3 million cases of diarrhea annually in the United States. The known risk factors of *C. difficile* infection (CDI) are exposure to antibiotics, advanced age, and residence in hospitals or long-term care facilities. The symptoms of CDI range from mild diarrhea to pseudomembranous colitis and toxic megacolon. The average cost of treatment is about $10,000 per case. The mortality rate of *Clostridium difficile* associated disease (CDAD) increased from 5.7 deaths per million population in 1999 to 23.7 deaths per million population in 2004 due to the emergence of hypervirulent outbreak strains. Accurate diagnosis is crucial for prompt and proper treatment of patients with CDI.

BRIEF DESCRIPTION OF THE DRAWINGS

Illustrative embodiments of the present invention are described in detail below with reference to the attached drawing figures, and wherein:

FIG. 1 depicts a sequence of Cwp84 from *C. difficile* strain 630;

DETAILED DESCRIPTION

Figures 2, 3, 4:
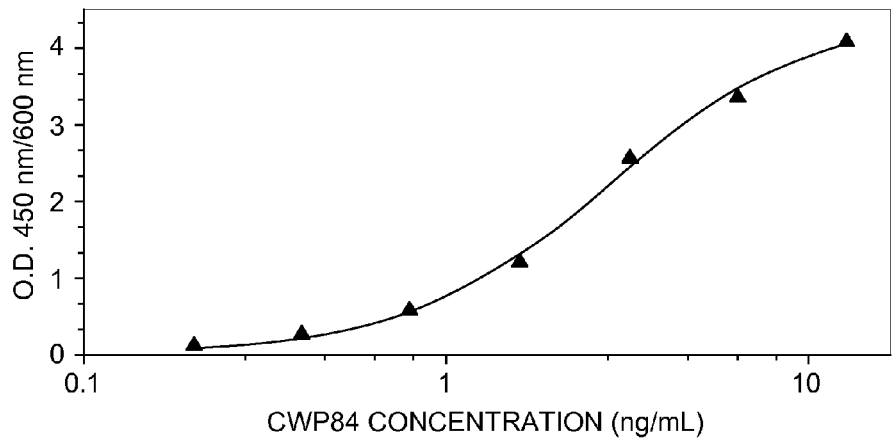
FIG. 2 depicts a graphical representation of a response curve of recombinant Cwp84 on anti-Cwp84 ELISA.
FIG. 3 depicts a tabular representation of a comparison between the number of positive (+) and negative (−) samples detected by anti-Cwp84 ELISA and ethanol shock culture method.
FIG. 4 depicts a tabular representation of a comparison between the number of positive (+) and negative (−) samples detected by an ELISA with both anti-GDH antibodies and anti-Cwp84 antibodies and an ELISA with anti-GDH antibodies alone.

The present invention is directed to test methods for detecting *C. difficile* in patients based on the presence of marker proteins derived from *C. difficile*. In particular, a new antigen marker, Cell Wall Protein 84 (Cwp84) may be used in immunoassays for the detection of *C. difficile*. Anti-Cwp84 antibodies could be used alone or in combination with antibodies against other *C. difficile* proteins, such as GDH (glutamate dehydrogenase) and Toxins A and B (i.e., TcdA and TcdB, respectively), in immunoassays for highly sensitive detection of *C. difficile*.

Generally, primary diagnostic methods for the detection of *C. difficile* in stool samples include plating samples on a selective medium, cytotoxicity assay, immunoassay and molecular assays such as polymerase chain reaction (PCR) based and isothermal DNA amplification. The presence of *C. difficile* in stool samples can be detected by selective culturing methods or immunoassays targeting a common antigen present in all *C. difficile* strains.

Presently, there are four major types of tests for detecting *C. difficile* in stool samples. The first, ethanol shock culture, includes treating fecal samples with ethanol followed by plating on cycloserine-cefoxitin-fructose agar (CCFA) and is considered the gold standard for its high sensitivity. However, this test may take up to 72 hours to obtain results and it does not differentiate between toxigenic and non-toxigenic strains of *C. difficile*.

Cytotoxicity test in tissue culture, the second type of test, can differentiate between toxigenic and nontoxigenic strains of *C. difficile* but the sensitivity is lower compared to PCR-based tests. Also, it takes up to 48 hours for a conclusion to be obtained using this test.

The third, DNA amplification-based tests, targets the toxin genes A or B and is highly sensitive but costly. There is also a concern that the presence of toxin genes does not necessarily correlate with the presence of amounts of toxin proteins that are relevant to the disease.

Lastly, antibody-based tests, such as enzyme-linked immunosorbent assays (ELISAs) and lateral flow tests, are rapid tests to detect the presence of Toxin A, Toxin B, and/or *C. difficile* common antigen glutamate dehydrogenase (GDH). GDH is an abundant metabolic enzyme which is highly conserved among *C. difficile* strains. The presence of GDH indicates the presence of *C. difficile* but does not differentiate between toxigenic and non-toxigenic strains. The immunoassays are rapid, cost effective, and can be used as point-of-care tests. Immunoassays detecting GDH are highly sensitive while immunoassays detecting toxins A and B show lower sensitivity compared to toxigenic culture method and molecular methods targeting toxin genes. Therefore, immunoassays based on *C. difficile* common antigens such as GDH serve as economical screening tests for the presence of *C. difficile* with follow-up testing used to confirm that TcdA and/or TcdB is present. One such approach is to use immunoassays as a screening test for the presence of common antigens such as GDH followed by more sensitive tests for the detection of toxins.

The sensitivity of antibody-based tests is influenced by multiple factors, such as interfering substances, the stability of the antigen analyzed and the variation of the amount of antigen produced by different *C. difficile* strains. The incorporation of antibodies against additional antigen markers that show less, or at least distinct patterns of, variability would help overcome these obstacles Several *C. difficile* proteins were examined as potential stand-alone or additional antigens in immunoassays, based on the criteria of being abundant, conserved among all sequenced *C. difficile* strains, and *C. difficile* specific. Preference was given to cell surface antigens, as these proteins are exposed on the surface of the bacteria and are accessible to the antibodies used in the assay. From among those candidate proteins, Cwp84, a cell surface protease and possible colonization factor, was selected.

*C. difficile* cells process a surface layer (S-layer) outside of the peptidoglycan layer. The S-layer is present in both vegetative cells and *C. difficile* spores, and proteins within the S-layer mediate host-pathogen interactions. Several *C. difficile* surface proteins bind to gastrointestinal tissues and are potential colonization factors. These proteins include flagellar proteins FliC and FliD, the heat shock protein GroEL, the fibronectin binding protein Fbp68, surface layer protein SlpA, and Cwp66.

Surface layer protein A (SlpA) is the major component of the surface layer of *C. difficile*. SlpA has to be post-translationally processed into a high molecular weight domain and a low molecular weight domain to be fully functional. There are two cysteine proteases located in the surface layer of *C. difficile*: CD2787 (Cwp84, NCBI accession number YP_001089300) and CD1751 (Cwp13, NCBI accession number YP_001088255). The absence of Cwp13 in a virulent *C. difficile* strain R20291 indicates that Cwp13 is not crucial for pathogenesis. In addition, the normal processing of SlpA in a cwp13 mutant confirms that Cwp13 is not involved in SlpA maturation. This leaves Cwp84 as the probable cysteine protease involved in the maturation of SlpA. The accumulation of unprocessed SlpA in cwp84 mutant strains further suggests that Cwp84 is responsible for the cleavage of SlpA.

Besides processing SlpA, Cwp84 may also be more directly involved in colonization of the intestine by *C. difficile*. The ability of *C. difficile* to express/release proteins that degrade host tissues contributes to its ability to colonize the intestinal epithelium. Cwp84 is not only associated with the S-layer but is also secreted. Cwp84 is active over a wide range of pH (3.5 to 8.0) with the optimum pH at 7.5 and is capable of degrading human fibronectin, laminin and vitronectin, proteins of the extracellular matrix. External protease activity has been observed in all *C. difficile* isolates examined and the protease activity can be neutralized by the cysteine protease specific inhibitor E64, suggesting that Cwp84, since it is the major cysteine protease of the S-layer, is responsible for this degradative activity.

The transcription, translation and post-translational modifications of Cwp84 have been characterized. The gene encoding Cwp84 is transcribed as a monocistronic message in the early exponential phase of growth. The location and maturation of Cwp84 requires multiple proteins. The secretion of Cwp84 to the S-layer involves the ATPases SecA1 or SecA2. Cwp84 is expressed as a proenzyme and the maturation of Cwp84 requires post translational modification. The mature Cwp84 is about 47 kDa. The post-translational modification of Cwp84 includes the removal of the signal peptide (amino acids 1-32), the removal of amino acids 33-91 by Cwp13 and autoproteolysis. Sequence analysis of Cwp84 reveals a C-terminal anchoring domain and an N-terminal protease domain that is homologous to cysteine proteases in other bacteria. Cysteine at position 116 is critical for the enzymatic activity of Cwp84, and activity can be abolished by a Cysteine 116 to Alanine (C116A) mutation. Illustrated in FIG. 1, and provided as SEQ ID NO 1, is an amino acid sequence from a sequenced *C. difficile* strain 630. Amino acids 1 to 32 are predicted to be a leader signal peptide. In the present embodiment, a portion of the Cwp84 sequence is used. In additional embodiments, full length of the Cwp84 sequence may be used.

In an embodiment of the present invention, a method of detecting *C. difficile* in stool samples using antibodies to Cwp84 is provided. Several characteristics of Cwp84 make it a good diagnostic marker. First of all, compared to other colonization factors, such as Cwp66 and SlpA, Cwp84 is more conserved among sequenced *C. difficile* strains, which makes it a better diagnostic marker for the detection of all *C. difficile* isolates. Secondly, Cwp84 is *C. difficile*-specific. No protein with significant homology is found in other bacteria. Most interestingly, the expression of Cwp84 is up-regulated if *C difficile* is exposed to certain antibiotics. Antibiotic exposure is the most important risk factor for CDAD. The usage of broad-spectrum antibiotics, such as clindamycin, aminopenicillins, cephalosporins and fluoroquinolones disturbs the normal gut flora and allows subsequent *C. difficile* infection. The expression of Cwp84 is induced by ampicillin and clindamycin in many clinical isolates and by fluoroquinolones in moxifloxacin-resistant *C. difficile* isolates. Among colonization factors tested, Cwp84 is the most up-regulated upon antibiotic treatment. This makes Cwp84 a good diagnostic marker for antibiotic treatment-related CDAD.

An embodiment of the present invention provides methods for using Cwp84, either independently or in combination with existing markers such as GDH, as a diagnostic marker for detecting CDI using fecal samples of humans. In this embodiment, humans present with symptoms common to *C. difficile* but have not yet been diagnosed. In additional embodiments, a person may be diagnosed with *C. difficile* infection upon identifying the presence of *C. difficile* in the fecal sample.

The present invention is directed to detection methods for using Cwp84 as an indicator for the presence of *C. difficile* in bacterial cultures or feces. An immunoassay such as ELISA, which utilizes either monoclonal or polyclonal antibodies to Cwp84, can be used to indicate the presence or absence of *C. difficile*. To produce antibodies against Cwp84, Cwp84 from *C. difficile* strain 630 was recombinantly expressed in *E. coli*. Polyclonal and monoclonal antibodies against the recombinant mutant Cwp84 were generated in goats and mice, respectively. An ELISA was developed using polyclonal anti-Cwp84 antibodies as capturing antibodies and horseradish peroxidase (HRP)-conjugated monoclonal anti-Cwp84 antibodies as detection antibodies.

In the ELISA, the fecal specimen is diluted 5-fold and added to a well containing the immobilized polyclonal antibodies. If the fecal specimen contains *C. difficile*, the Cwp84 produced by *C. difficile* will bind to the antibodies during the incubation at 37° C. Following the incubation, monoclonal antibodies coupled to horseradish peroxidase (HRP conjugate) are added and allowed to bind to the captured Cwp84. Unbound conjugate is then washed away from the well and substrate (tetra-methyl-benzidene and hydrogen peroxide) is added for color development. Following the substrate incubation, 0.1 M sulfuric acid is added to quench the reaction and an optical density (OD) at 450 nM is measured using a spectrophotometer. An OD reading equal or above 0.080 indicates the presence of *C. difficile* and an OD less than 0.080 indicates the absence of *C. difficile* in the fecal specimen.

This ELISA can also be used to distinguish bacterial cultures of *C. difficile* from cultures of other types of bacteria. Bacterial cultures can be diluted 20-fold in phosphate buffered saline (PBS) and added to a well coated with polyclonal antibodies against Cwp84. If the culture tested contains *C. difficile*, the Cwp84 produced by *C. difficile* cells will bind to the immobilized polyclonal antibodies during the incubation at 37° C. Following the incubation, monoclonal antibodies conjugated with HRP are added as the detection antibodies. After the unbound detection antibodies are washed away, substance is added for color development followed by the quenching of the reaction by 0.1 M sulfuric acid. The OD at 450 nM is then measured using a spectrophotometer. An OD reading equal to or above 0.080 indicates the presence of *C. difficile* and an OD less than 0.080 indicates the absence of *C. difficile* in the bacterial culture.

To study the detection limit of the ELISA using polyclonal anti-Cwp84 antibodies as capturing antibodies and monoclonal anti-Cwp84 antibodies conjugated to HRP as detection antibodies, Cwp84 was expressed in *E. coli*, purified and diluted to concentrations shown in Table 1. A four parameter logistics curve fit method was used to generate the response curve shown in FIG. 2. Using OD 0.080 as a cutoff, 0.2 ng/mL Cwp84 can be detected by this ELISA.

TABLE 1

Detection Limit of Recombinant Cwp84 on anti-Cwp84 ELISA

| Concentration of Cwp84 (ng/mL) | OD 450 nm/600 nm |
|---|---|
| 0 | 0.003 |
| 0.2 | 0.114 |
| 0.4 | 0.268 |
| 0.8 | 0.567 |
| 1.6 | 1.207 |
| 3.2 | 2.572 |
| 6.4 | 3.363 |
| 12.8 | 4.104 |

EXAMPLE 1

To investigate whether or not Cwp84 can be used as a marker to detect frequently seen strains of *C. difficile*, twelve *C. difficile* strains of prevalent ribotypes were tested using the anti-Cwp84 ELISA. The PCR ribotyping method is relatively easy to perform, reproducible, and is the most discriminatory method to differentiate and identify *C. difficile* strains.

Results

Twelve *C. difficile* strains of prevalent ribotypes were inoculated into Brain-heart infusion broth (BHI; Oxoid). Cultures were grown at 37° C. over night under anaerobic conditions. The *C. difficile* strains in BHI cultures were diluted 1:20 in PBS and tested on an ELISA using polyclonal anti-Cwp84 antibodies as capturing antibodies and monoclonal anti-Cwp84 antibodies-HRP conjugate as detection antibodies. The absorbance on dual wavelength (OD450/620 nm) is shown in Table 2. The cutoff of this ELISA was set to be 0.080. All the ribotypes produced strongly positive reactions on this ELISA, indicating that the Cwp84 ELISA can be used for detecting many common toxigenic and non-toxigenic strains of *C. difficile*.

TABLE 2

Twelve Prevalent *C. difficile* Strains Produce Positive Reactions on anti-Cwp84 ELISA

| Ribotype | Toxigenic | OD 450/620 nm | Interpretation |
|---|---|---|---|
| 001 | YES | 0.837 | + |
| 002 | YES | 0.228 | + |
| 003 | YES | 0.826 | + |
| 005 | YES | 3.882 | + |
| 009 | NO | 1.123 | + |
| 010 | NO | 0.649 | + |
| 014 | YES | 0.591 | + |
| 015 | YES | 1.143 | + |
| 027 | YES | 0.936 | + |
| 039 | NO | 0.720 | + |
| 053 | YES | 0.876 | + |
| 106 | YES | 1.906 | + |

EXAMPLE 2

To investigate whether or not other bacteria are cross-reactive on the anti-Cwp84 ELISA, fifty-six strains of bacteria that are commonly found in feces or closely related to *C. difficile* phylogenetically were grown under required conditions and tested on the anti-Cwp84 ELISA using polyclonal anti-Cwp84 antibodies as capturing antibodies and monoclonal anti-Cwp84 antibodies conjugated to HRP as detection antibodies. The absorbance using dual wavelength detection (OD 450/620 nm) is shown in Table 3. The cutoff of this ELISA was set to be 0.080. The negative reaction produced by all of the bacteria tested on this ELISA indicated no cross-reactivity on the anti-Cwp84 ELISA.

TABLE 3

No cross-reaction with anti-Cwp84 ELISA

| Bacterium | Strain | Optical Density | Interpretation |
|---|---|---|---|
| Aeromonas hydrophila | ATCC 35654 | 0.001 | − |
| Bacillus cereus | ATCC 14579 | 0.005 | − |
| Bacillus subtilis | ATCC 6051 | 0.001 | − |
| Bacteroides fragilis | VPI 13785 | 0.002 | − |
| Campylobacter coli | ATCC 43478 | 0.003 | − |
| Campylobacter jejuni | ATCC 29428 | 0.006 | − |
| Candida albicans | ATCC 10231 | 0.001 | − |
| Citrobacter freundii | ATCC 8090 | 0.009 | − |
| Clostridium bifermentans | ATCC 638 | 0.005 | − |
| Clostridium clostridiforme | VPI 316 | 0.001 | − |
| Clostridium butyricum | ATCC 8260 | 0.004 | − |
| Clostridium glycolicum | VPI 2048 | 0.001 | − |
| Clostridium innocuum | ATCC 14501 | 0.004 | − |
| Clostridium ghonii | ATCC 25757 | 0.002 | − |
| Clostridium haemolyticum | VPI 2041 | 0.002 | − |
| Clostridium histolyticum | ATCC 19401 | 0.002 | − |
| Clostridium novyi | VPI 5771 | 0.002 | − |
| Clostridium perfringens | NCIB 10748 | 0.002 | − |
| Clostridium septicum | VPI 3533 | 0.002 | − |
| Clostridium sordellii | VPI 9048 | 0.004 | − |
| Clostridium sordellii | VPI 7319 | 0.001 | − |
| Clostridium sporogenes | VPI 9743 | 0.001 | − |
| Enterobacter aerogenes | ATCC 13048 | 0.002 | − |
| Enterobacter cloacae | ATCC 13047 | 0.002 | − |
| Enterococcus faecalis | ATCC 19433 | 0.003 | − |
| Escherichia coli EIEC | ATCC 43893 | 0.001 | − |
| Escherichia coli | ATCC 11775 | 0.000 | − |
| Escherichia coli O157 H7 | ATCC 43895 | 0.002 | − |
| Escherichia coli O157 H7 (non-tox) | ATCC 43888 | 0.003 | − |
| Escherichia coli ETEC | ATCC 35401 | 0.005 | − |
| Escherichia coli EPEC | ATCC 12014 | 0.002 | − |
| Escherichia fergusonii | ATCC 35469 | 0.005 | − |
| Escherichia hermannii | ATCC 33650 | 0.003 | − |
| Gardnerella vaginalis | ATCC 14019 | 0.002 | − |
| Helicobacter pylori | ATCC 43504 | 0.003 | − |
| Klebsiella pneumoniae | ATCC 9997 | 0.003 | − |
| Peptostreptococcus anaerobius | ATCC 27337 | 0.002 | − |
| Proteus vulgaris | ATCC 8427 | 0.002 | − |
| Providencia stuartii | ATCC 33672 | 0.003 | − |
| Pseudomonas aeruginosa | ATCC 10145 | 0.001 | − |
| Pseudomonas fluorescens | ATCC 13525 | 0.002 | − |
| Salmonella enterica serovar minnesota | ATCC 49284 | 0.004 | − |
| Salmonella typhimurium | ATCC 14028 | 0.002 | − |
| Serratia liquefacians | ATCC 27592 | 0.002 | − |
| Shigella dysenteriae | ATCC 13313 | 0.005 | − |
| Shigella flexneri | ATCC 29903 | 0.002 | − |
| Shigella sonnei | ATCC 11060 | 0.002 | − |
| Staphylococcus aureus | ATCC 6358 | 0.002 | − |
| Staphylococcus aureus (Cowans) | ATCC 12598 | 0.003 | − |
| Staphylococcus epidermidis | ATCC 27626 | 0.002 | − |
| Vibrio cholerae | ATCC 14035 | 0.012 | − |
| Vibrio parahaemolyticus | ATCC 17802 | 0.006 | − |
| Stenotrophomonas maltophilia | ATCC 13637 | 0.002 | − |
| Yersinia enterocolitica | ATCC 23715 | 0.002 | − |

EXAMPLE 3

To investigate whether Cwp84 can be used as a diagnostic marker to detect *C. difficile* in fecal samples, 64 clinical fecal samples were tested using the anti-Cwp84 ELISA described above. The sensitivity and specificity of the anti-Cwp84 ELISA for the detection of *C. difficile* were calculated using an ethanol shock culture method as the gold standard.

Results

The anti-Cwp84 ELISA detected twenty-nine (29) positive samples out of the thirty-four (34) positive samples identified by the ethanol shock culture method. All thirty (30) samples that tested negative by anti-Cwp84 ELISA were true negative samples that failed to grow using the ethanol shock culture method. Thus, the calculated sensitivity and specificity of the anti-Cwp84 ELISA were 85% and 100%, respectively.

FIG. 3 illustrates the results of anti-Cwp84 ELISA on 64 human fecal samples compared to the results of ethanol shock culture method. Anti-Cwp84 ELISA detected the presence of *C. difficile* in 29 of the 34 positive samples determined by ethanol shock culture method.

EXAMPLE 4

To investigate whether Cwp84 can be used in combination with GDH as common antigens to indicate the presence of *C. difficile* in fecal samples, an ELISA was developed using a combination of both anti-Cwp84 polyclonal antibodies and anti-GDH antibodies as capturing antibodies and HRP conjugated anti-Cwp84 monoclonal antibodies and HRP conjugated anti-GDH monoclonal antibodies as detection antibodies. Forty-five clinical samples that had been determined to be positive for *C. difficile* by the ethanol shock culture method, but that showed either weak or negative results on a standard anti-GDH ELISA, were selected and tested on the ELISA containing antibodies against both Cwp84 and GDH.

Results

Five of the 25 samples that were negative by single antibody anti-GDH ELISA were positive on the ELISA utilizing both anti-GDH and anti-Cwp84 antibodies. The combination of anti-Cwp84 antibodies with anti-GDH antibodies in the ELISA increased the sensitivity of the assay. The addition of anti-Cwp84 antibodies as both capturing antibodies and detection antibodies helped to detect the presence of *C. difficile* in stool samples that was missed in ELISAs utilizing anti-GDH antibodies alone.

FIG. 4 illustrates the results of this example. Forty-five fecal samples determined to be *C. difficile* positive by the ethanol shock culture method, but that were weak or negative on the anti-GDH ELISA, were tested using the ELISA with both anti-GDH antibodies and anti-Cwp84 antibodies. The combination of both anti-GDH and anti-Cwp84 antibodies detected *C. difficile* in 5 additional samples that had tested negative by ELISA with anti-GDH antibodies only.

In summary, the present invention provides Cwp84 as an additional diagnostic marker for detecting *C. difficile* in stool samples in addition to the existing diagnostic markers GDH, Toxin A, and Toxin B. The examples and embodiments of the present invention have been described in relation to particular embodiments which are intended in all respects to be illustrative rather than restrictive. Alternative embodiments will become apparent to those skilled in the art to which the present invention pertains without departing from its scope.

Embodiments of the present invention also provide a device to test a fecal sample obtained from a person and use Cwp84 as an indicator of *C. difficile*. Broadly speaking, the device of the invention comprises any configuration of components that permit practice of the method of the invention. More specifically, the device of the invention comprises any configuration of components that permit a sample containing, or suspected of containing, a substance of interest to be retained in a pre-defined area or region of the device, where the area or region comprises a specific binding pair member that is specific, either directly or indirectly, for the substance.

In its most basic form, the device of the invention comprises (1) a receiving portion to receive a fecal sample from a person and (2) a testing portion to detect the presence of Cwp84 of the fecal sample, where the testing portion comprises a specific binding pair member that is specific for Cwp84. Any additional components that permit the practice of the method of the invention may also be included in the device.

From the foregoing, it will be seen that this invention is one well adapted to attain all the ends and objects herein above set forth together with other advantages which are obvious and which are inherent to the method. It will be understood that certain features and subcombinations are of utility and may be employed without reference to other features and subcombinations. This is contemplated by and is within the scope of the claims.

---

What the invention claimed is:

1. A method for testing a fecal sample from a person, the method comprising:
    obtaining the fecal sample from the person;
    determining whether Cell Wall Protein 84 (Cwp84) is present in the fecal sample;
    upon determining Cwp84 is present in the fecal sample, concluding the presence of *C. difficile* in the fecal sample; and
    diagnosing the person with active *C. difficile* infection upon determining the presence of *C. difficile* in the fecal sample.

2. The method of claim 1, wherein the presence of *C. difficile* may be further concluded based upon the presence of glutamate dehydrogenase (GDH) and toxins A and B in the fecal sample.

3. The method of claim 1, wherein the presence of Cwp84 is identified using enzyme-linked immunosorbent assays.

4. The method of claim 3, wherein one or more antibodies against Cwp84 are raised against a native Cwp84 purified from *C. difficile* strains.

5. The method of claim 3, wherein one or more antibodies against Cwp84 are raised against Cwp84 recombinantly expressed in *E. coli*.

6. The method of claim 1, wherein the presence of Cwp84 is identified using lateral flow techniques and immunochemical reactions on a membrane.

7. The method of claim 6, wherein one or more antibodies against Cwp84 are raised against a native Cwp84 purified from *C. difficile* strains.

8. The method of claim 6, wherein one or more antibodies against Cwp84 are raised against Cwp84 recombinantly expressed in *E. coli*.

9. The method of claim 3, wherein one or more antibodies against Cwp84 are raised against a full length sequence of Cwp84.

10. The method of claim 3, wherein one or more antibodies against Cwp84 are raised against one or more variants of Cwp84 from one or more *C. difficile* isolates.

11. The method of claim 3, wherein one or more antibodies against Cwp84 are raised against one of active Cwp84 or inactive Cwp84 containing one or more mutations.

12. The method of claim 11, wherein the one or more mutations include C116A.

13. The method of claim 2, wherein the presence of GDH and Toxins A and B is measured using one or more of enzyme-linked immunoassays, lateral flow, and immunochemical reactions on a membrane.

14. A method for testing a fecal sample from a person, the method comprising:
    obtaining the fecal sample from the person;
    determining whether *C. difficile* is present in the fecal sample based on the presence of Cell Wall Protein 84 (Cwp84) and glutamate dehydrogenase (GDH);
    upon determining the presence of either GDH or Cwp84 in the fecal sample, concluding presence of *C. difficile* in the fecal sample; and
    diagnosing the person with active *C. difficile* infection upon determining the presence of *C. difficile* in the fecal sample.

15. The method of claim 14, further comprising identifying the presence of Toxin A and Toxin B in the fecal sample, wherein the presence of Cwp84, GDH, and Toxins A and B is identified utilizing at least one of enzyme-linked immunoassays, lateral flow, and immunochemical reactions on a membrane.

16. The method of claim 15, wherein one or more antibodies against Cwp84 are raised against one of a full length sequence of Cwp84.

17. The method of claim 15, wherein one or more antibodies against Cwp84 are raised against one of active Cwp84 or inactive Cwp84 containing a C116A mutation.

* * * * *